United States Patent
Boday et al.

(10) Patent No.: US 10,316,161 B2
(45) Date of Patent: Jun. 11, 2019

(54) METHOD OF MAKING HIGHLY POROUS POLYHEXAHYDROTRIAZINES CONTAINING ANTIMICROBIAL AGENTS

(71) Applicant: International Business Machines Corporation, Armonk, NY (US)

(72) Inventors: Dylan J. Boday, Tucson, AZ (US); Mareva B. Fevre, San Jose, CA (US); Jeannette M. Garcia, San Leandro, CA (US); James L. Hedrick, Pleasanton, CA (US); Jason T. Wertz, Pleasant Valley, NY (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 77 days.

(21) Appl. No.: 15/461,430

(22) Filed: Mar. 16, 2017

(65) Prior Publication Data
US 2018/0265664 A1    Sep. 20, 2018

(51) Int. Cl.
*C08J 9/28* (2006.01)
*A01N 59/16* (2006.01)
*C08G 73/02* (2006.01)

(52) U.S. Cl.
CPC ............ *C08J 9/286* (2013.01); *A01N 59/16* (2013.01); *C08G 73/024* (2013.01); *C08J 2201/052* (2013.01); *C08J 2205/026* (2013.01); *C08J 2379/04* (2013.01); *Y02P 20/544* (2015.11)

(58) Field of Classification Search
CPC ........ C08G 73/0644; C08G 2101/0091; C08G 73/02–73/028; C08J 2379/02–2379/06
See application file for complete search history.

(56) References Cited

U.S. PATENT DOCUMENTS 4,061,750 A * 12/1977 Lada .................. A01N 43/64
                                                    514/241
4,839,460 A    6/1989 Molzahn
5,086,085 A    2/1992 Pekala
(Continued)

FOREIGN PATENT DOCUMENTS

CN    101661839 B    2/2012
CN    103073891 A    5/2013
(Continued)

OTHER PUBLICATIONS

Garcia et al, "Recyclable Strong Thermosets and Organogels Via Parafomaldehyde Condensation with Diamines", Science Magazine, May 2014, vol. 344, pp. 732-735.
(Continued)

*Primary Examiner* — Michael M Dollinger
*Assistant Examiner* — Christina H Wales
(74) *Attorney, Agent, or Firm* — Patterson + Sheridan, LLP

(57) ABSTRACT

Materials and methods are described herein that include forming a porous polymer network with antimicrobial and antifouling properties. The antifouling portion may be a polymer, such as polyethylene glycol, and the antimicrobial portion may be a metal, or a different cationic species, such as a quaternary ammonium salt. The method generally includes forming a reaction mixture comprising a formaldehyde, a bridging group, and moieties with antifouling and antimicrobial properties.

12 Claims, 2 Drawing Sheets

(56) References Cited

U.S. PATENT DOCUMENTS

| | | | |
|---|---|---|---|
| 5,543,516 A | 8/1996 | Ishida | |
| 6,224,983 B1 | 5/2001 | Sodervall et al. | |
| 6,670,402 B1 | 12/2003 | Lee et al. | |
| 7,071,287 B2 | 7/2006 | Rhine et al. | |
| 7,074,880 B2 | 7/2006 | Rhine et al. | |
| 8,318,698 B2 | 11/2012 | Lee et al. | |
| 9,271,498 B2 | 3/2016 | Boday et al. | |
| 9,777,116 B2 * | 10/2017 | Boday | C08G 73/065 |
| 2003/0134916 A1 | 7/2003 | Hrubesh | |
| 2006/0178443 A1 | 8/2006 | Boinowitz et al. | |
| 2010/0144913 A1 | 6/2010 | Alteheld et al. | |
| 2010/0180413 A1 | 7/2010 | Jeong | |
| 2010/0210810 A1 | 8/2010 | Katagiri et al. | |
| 2010/0288160 A1 | 11/2010 | Maisels et al. | |
| 2010/0310847 A1 | 12/2010 | Suh et al. | |
| 2011/0171280 A1 * | 7/2011 | Toreki | D06M 11/155 424/411 |
| 2011/0245362 A1 | 10/2011 | Hwang et al. | |
| 2012/0142800 A1 * | 6/2012 | Fricke | C08G 18/10 521/163 |
| 2012/0231251 A1 * | 9/2012 | Kim | C08K 3/346 428/219 |
| 2015/0104579 A1 * | 4/2015 | Hedrick | C08G 65/00 427/385.5 |
| 2016/0108176 A1 | 4/2016 | Boday et al. | |
| 2017/0114186 A1 | 4/2017 | Boday et al. | |

FOREIGN PATENT DOCUMENTS

| | | |
|---|---|---|
| CN | 105645382 A | 6/2016 |
| WO | 0226849 A1 | 4/2002 |

OTHER PUBLICATIONS

E. Frackowiak, F. Béguin, "Carbon Materials for the Electrochemical Storage of Energy in Capacitors" Carbon, vol. 39, pp. 937-950, (2001).

C. Moreno-Castilla, F.J. Maldonado-Hódar, "Carbon Aerogels for Catalysis Applications: An Overview," Carbon, vol. 43, pp. 455-465, (2005).

* cited by examiner

US 10,316,161 B2

METHOD OF MAKING HIGHLY POROUS POLYHEXAHYDROTRIAZINES CONTAINING ANTIMICROBIAL AGENTS

BACKGROUND

Materials and methods described herein relate to modified porous poly(hexahydrotriazine) (PHT) polymers.

Hospital acquired infections, nosocomial infections, affect about 10% of all hospital patients in the United States, resulting in nearly 100,000 deaths annually. Consequently, considerable efforts are dedicated to developing antimicrobial surfaces and filtration methods to prevent the spreading of microorganisms in a clinical setting. One method of preparing antimicrobial surfaces involves the use of silver nanoparticles, a well-known particle capable of efficient contact killing of microorganisms. Furthermore, the ability to produce nanoparticles at a surface/interface offers applications well beyond a clinical setting to include applications in the fields of catalysis, photonics and sensors. Antibacterial filters and coatings using metal-based (i.e., silver-based) technologies however suffer several shortcomings including, just to name a few, long-term antibacterial performances and stability, development of bacterial resistance, or scalability to an industrial setting. Therefore, an improved filter or coating is needed.

SUMMARY

Embodiments described herein relate to methods of making porous and nanoporous PHTs with antimicrobial and antifouling properties.

In an embodiment, a porous polymer is provided. The porous polymer comprises a plurality of hexahydrotriazine units, hemiaminal units, or a combination thereof, forming a polymer network; and an antifouling component covalently linked to the polymer network, an antimicrobial component chemically linked to the polymer network, or a combination thereof.

In another embodiment, the porous polymer is an aerogel.

In an embodiment, a method of forming a porous polymer is provided. The method includes exposing a diamine or triamine monomer and an amine terminated precursor to an aldehyde material; forming a material comprising a polyheminal, a polyhexahydrotriazine, or a combination thereof; subjecting the polymer to a supercritical $CO_2$ solvent removal process; thermally hardening the polymer to form an aerogel; and immersing the aerogel in a solution containing metal ions.

In another embodiment, a method of forming an antimicrobial and antifouling polyhexahydrotriazine material is provided. The method includes forming a polyhexahydrotriazine polymer in a solvent; forming a polyhexahydrotriazine aerogel by removing the solvent.

In another embodiment, a method of forming an antimicrobial and antifouling polyhexahydrotriazine material is provided. The method includes forming a polyhexahydrotriazine polymer in a solvent; forming a polyhexahydrotriazine aerogel by removing the solvent; immersing the polyhexahydrotriazine aerogel in a solution containing metal ions; and nucleating the metal ions at porous surfaces of the polyhexahydrotriazine aerogel to form metallic nanoparticles.

DETAILED DESCRIPTION

Figure 1:
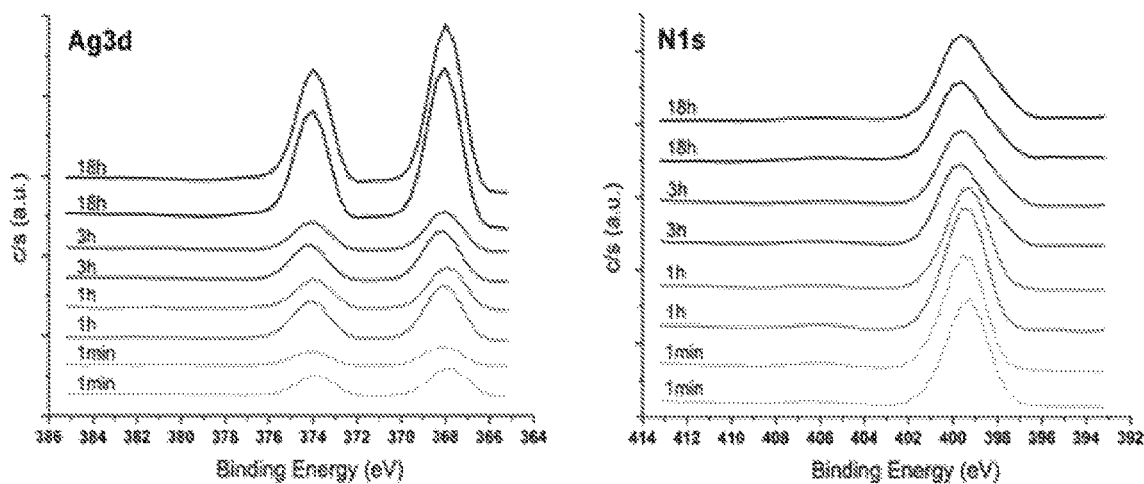
FIG. 1 shows a series of X-ray photoelectron spectrographs (XPS) of the surface of a PHT material dipped in a AgOTf solution for 1 minute, 1 hour, 3 hours and 18 hours.

Methods of forming porous polymers are described herein that include forming a porous polymer network containing poly(hexahydrotriazine) (PHTs), poly(hemiaminals) (PHAs), or combinations of both, and integrating antifouling and antimicrobial agents into the porous polymer network. Antimicrobial agents include metal nanoparticles such as silver, gold, copper, zinc, or any suitable metal nanoparticles, as well as cationic species such as quaternary ammonium salts and cationic polymers. Antifouling agents include polyethers (i.e., polyethylene glycol, also known as "PEG"), polyacrylates, polyepoxides, fluoropolymers, or a combination thereof. The method generally includes forming a porous polymer, such as PHA or PHT, or a combination of both, by reaction of an amine, a bridging group, and a formaldehyde (i.e., formaldehyde or paraformaldehyde), optionally in the presence of a solvent, at an elevated temperature.

The porous polymer may be immersed in solutions of metal ions (such as silver, gold, zinc, copper, and other transition metals). The metal salts are placed in solution, and the metal salt solutions may contain any suitable solvent, such as dichloromethane, acetonitrile, or mixtures thereof. The metal salts can be made from any counterion including triflates, halides, nitrates, sulfates, citrates, and acetates. Such exposure leads to nucleation of metal nanoparticles at the surface of the porous polymer. Porous materials, such as aerogels, have high surface area for incorporating metal ions and for contacting materials to be treated using the porous material.

The porous polymer may be made by reaction of amine functionalized polymers such as polyethers (i.e., PEG), polyacrylates, polyepoxides, fluoropolymers, or combinations thereof, for example monofunctional amino PEG, a bridging group, and a formaldehyde (i.e., formaldehyde or paraformaldehyde), optionally in the presence of a solvent, at an elevated temperature. The amine functionalized polymer may be monofunctional, bifunctional, or multifunctional, or a mixture thereof.

The porous polymer may also be made by reacting precursors functionalized to include quaternary ammonium moieties with a bridging group and a formaldehyde (i.e., formaldehyde or paraformaldehyde), optionally in the presence of a solvent, at an elevated temperature. The precursors may be quaternary ammonium containing di-aromatic amines.

The porous polymer may be an organogel or an aerogel, such as a soft aerogel or a hardened aerogel. The benefit of using porous materials, such as aerogels, is the high surface area where the antifouling and antimicrobial moieties can be found.

The porous polymer may be formed by processing an organogel into an aerogel. The organogel is subjected to a solvent removal process that preserves the morphology of the solvent-swelled polymer in a dry form, thus forming an aerogel. The aerogel may then be thermally treated to harden the aerogel.

HTs and PHTs have the ability to bind antimicrobial metals. Moreover, the synthetic diversity of PHT and PHTrelated materials allow covalent incorporation of antimicrobial moieties, such as quaternary ammonium salts, and antifouling moieties, such as PEG, into the polymer network. The PHT materials can achieve a dual action of defending against bacterial adhesion and attacking any that bind, by incorporating combinations of antimicrobial and antifouling agents. By tailoring the amount of antimicrobial and antifouling moieties within the polymer, the responsiveness and the materials' properties may be altered depending on the application of use. In addition to the variety of applications for antimicrobial and antifouling materials, PHT polymers offer several advantages over conventional thermosets due to their ability to be recycled and the ability to have improved mechanical properties.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, enantiomers, of the represented compounds.

Numbered chemical structures are numbered using numbers, or numbers and letters, in parentheses. Numbered chemical reaction schemes are numbered using numbers, or numbers and letters, in square brackets. Unless otherwise noted, chemical reactions are performed at ambient conditions or under slight heating with no special atmosphere or head space, and may be performed using standard organic solvents to manage mix properties such as viscosity and flow index.

Generally, the polymers referred to herein can have the structure:

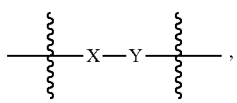

where X has the structure

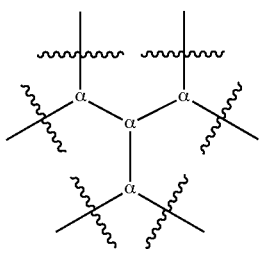

and Y may have the structure

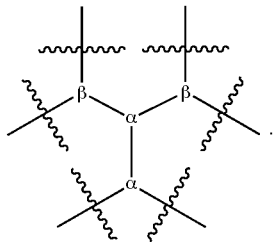

Each α and β may be further linked to another α and/or β. The symbols α and β represent polymer portions with different functionalities. In addition, the polymers referred to herein can be made entirely of X or entirely of Y.

Such polymers may be used to form porous and nanoporous materials by forming a polymer network of the first and second portions in any desired amounts. Here, the first portion α is shown as a trivalent group, but α may have any effective valence from 3 to 6, as further described below.

The first portion α may be a PHA or PHT polymer group. A PHT is a polymer that includes a plurality of trivalent hexahydrotriazine (HT) groups having the structure

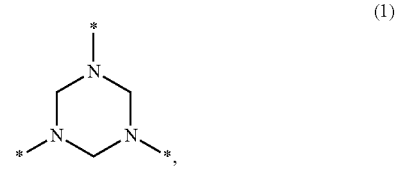

covalently linked to a plurality of bridging groups

wherein y' is 2 or 3, and K' is a divalent or trivalent radical. Bridging groups include moieties arising from diamine or triamine monomers. In this disclosure, starred bonds represent attachment points to other portions of the chemical structure. Each starred bond of a given HT group is covalently linked to a respective one of the bridging groups. Additionally, each starred bond of a given bridging group is covalently linked to a respective one of the HT groups. Thus, in some cases, a is an HT group as in structure (1).

A PHA is a polymer that includes a plurality of trivalent hemiaminal (HA) groups having the structure

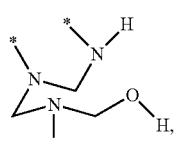

covalently linked to a plurality of the bridging groups of formula (2). Thus, in some cases, a is an HA group as in structure (3). It should be noted that each instance of a may be different in a single molecule, and in some cases a single molecule could have two or more different versions of a having valence of 3 to 6.

In one example, a PHA can be represented by the structure

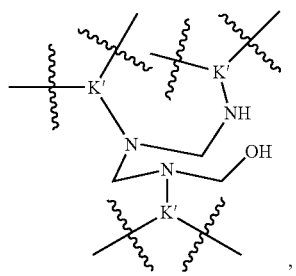

(4)

wherein the bridging groups K' are trivalent (y'=3 in formula 2). In this example, the first portion α is a hexavalent PHA. Similarly, a PHT can be represented by the structure

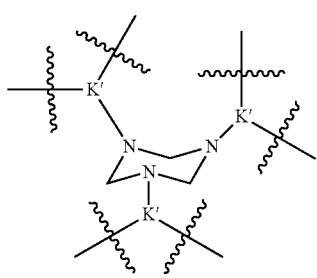

(5)

and in such an example the first portion α is a hexavalent PHT. In the case of divalent bridging groups K' (y'=2 in formula 2), the first portion α may have either, or both, of the following structures

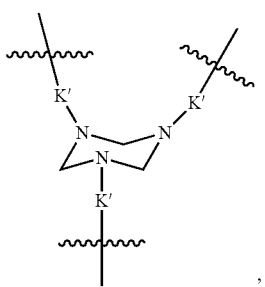

(6)

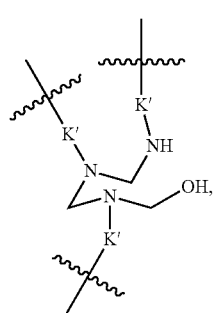

(7)

wherein the structure of formula (6) is a PHT structure and the structure of formula (7) is a PHA structure. The first portions α of formulas (6) and (7) are trivalent. Using a mixture of divalent and trivalent bridging groups K', the first portion α, which may be a PHT structure or a PHA structure, may have valence from 3 to 6.

Trivalent bridging groups K' that may be part of a porous network include the following structures:

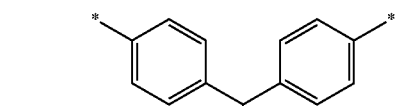

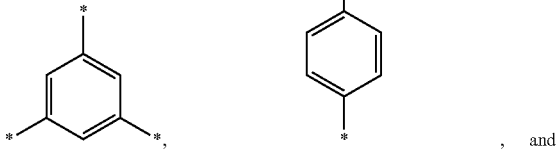

, and

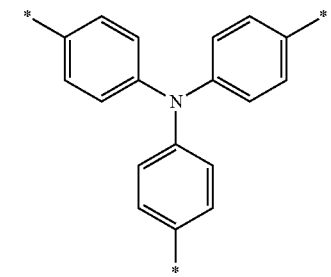

These structures may be included in the network by adding primary amine terminated molecules containing these structures to the reaction mixture with other primary amines and diamines, and a formaldehyde. Such structures may be included to increase non-porogen network bonding and density.

The second portion β may have valence from 1 to 3, and may be a polymer that is partially or fully degradable at elevated temperatures or under basic conditions. The second portion β may be a linear or quasi-linear polymer group, or the second portion β may have a cyclic center such as an HA or HT center. The second portion β may be a monovalent substituent group, a divalent bridging group, or a trivalent network group.

Examples of substituent groups that may be covalently linked to the second portion β may be a cationic species such as a quaternary ammonium, or amino functionalized polymers such as polyethers (i.e., PEG), polyacrylates, polyepoxides, fluoropolymers, or combinations thereof. The covalently-linked substituent group may also be a group that has antimicrobial or antifouling properties. Specifically, the covalently-linked substituent group may be an antimicrobial or antifouling moiety that is amino functionalized.

The second portion β may be a divalent bridging group with a PHT or PHA core and a monovalent substituent. The second portion β may also be a divalent bridging group with a PHT or PHA core, a divalent substituent, and a monovalent diluent group. Divalent bridging groups with PHT and PHA cores, respectively, and monovalent substituents have the general structures (8)

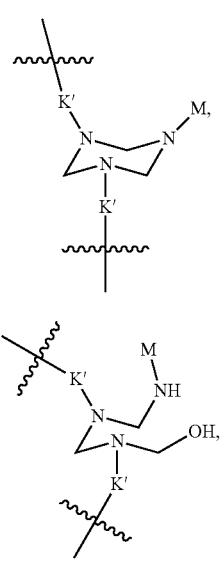

(9)

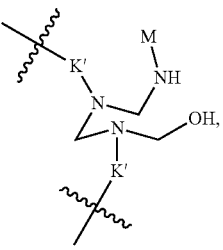

wherein M is a monovalent substituent, which may be any convenient small molecule or polymer that may be functionalized with a primary amine group, for example monofunctional amino PEG. A divalent linkage with PHT and PHA cores, respectively, and divalent substituents have the general structures (10)

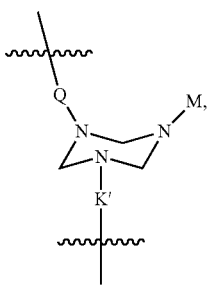

(11)

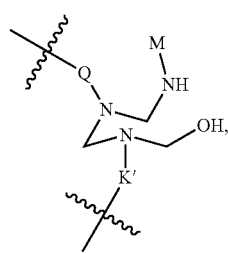

wherein M is a monovalent substituent that may be unreactive, acid degradable, base degradable, and/or thermally degradable, and Q is a divalent bridging group.

Other monovalent substituents that may be used as the monovalent substituent M include groups having the structures of the following formula:

(12)

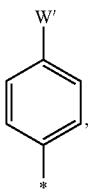

(13)

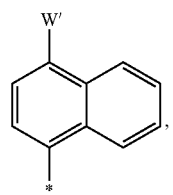

(14)

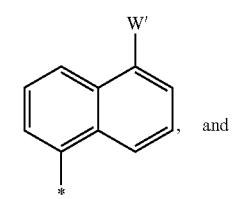

, and (15)

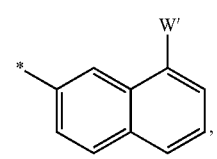

wherein W' is a monovalent radical selected from the group consisting of —N(R$^1$)(R$^2$), —OR$^3$, —SR$^4$, wherein R$^1$, R$^2$, R$^3$, and R$^4$ are independent monovalent radicals comprising at least one carbon. The starred bond is linked to a nitrogen of a hemiaminal group or a hexahydrotriazine group. Non-limiting exemplary monovalent groups having the structures of formulae 12-15 include:

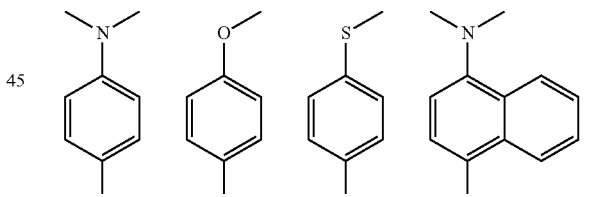

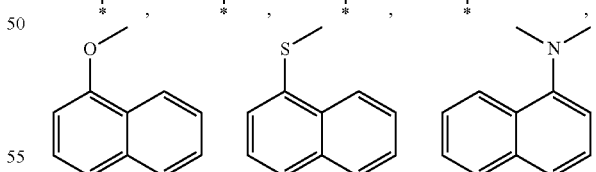

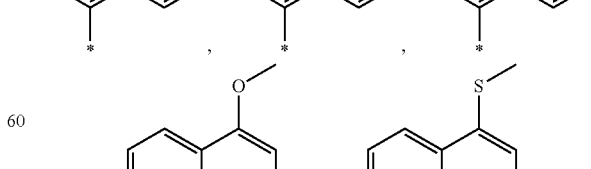

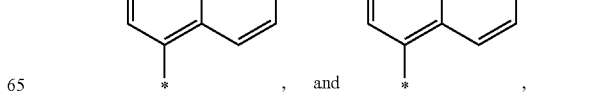

wherein the starred bond is linked to a nitrogen of a hemiaminal group or a hexahydrotriazine group. Monovalent groups can be used singularly or in combination.

Non-limiting exemplary monomers that give rise to monovalent groups in a porous network include N,N-dimethyl-p-phenylenediamine (DPD), p-methoxyaniline (MOA), p-(methylthio)aniline (MTA), N,N-dimethyl-1,5-diaminonaphthalene (15DMN), N,N-dimethyl-1,4-diaminonaphthalene (14DMN), and N,N-dimethylbenzidene (DMB), which have the following structures:

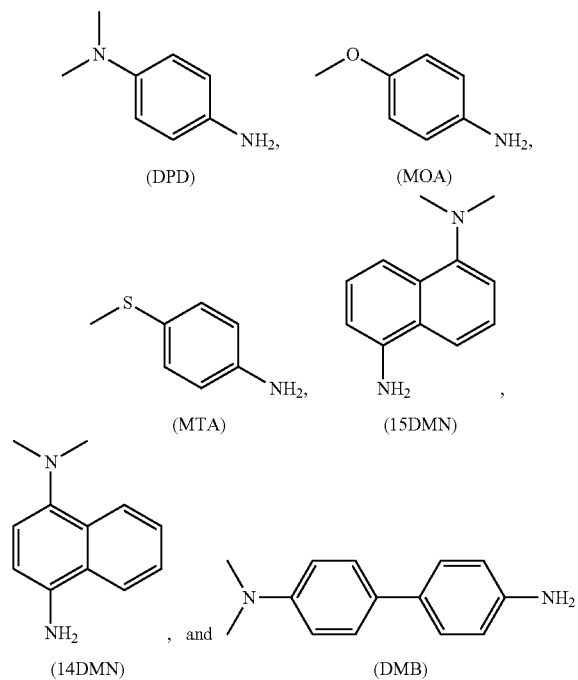

Some embodiments described herein are polymer networks having a PHA or PHT core, or a mixture thereof. Polymers having a PHA or PHT core are generally made by reacting a primary amine, or mixture thereof, with formaldehyde or oligomers thereof. The amino group of the primary amine reacts with the aldehyde to form a cyclic trimer that is a hydrogenated triazine. If a primary diamine is included, the diamine may cyclotrimerize at both ends to form the PHA or PHT network. In one example, 4,4'-oxydianiline is mixed with paraformaldehyde and heated to about 50° C. to form a PHA network. Further heating up to 200° C. forms a PHT network. The PHA network may be non-covalently bonded with water through hydrogen bonding, or with another solvent. A PHA complex with water has the general structure of formula (16)

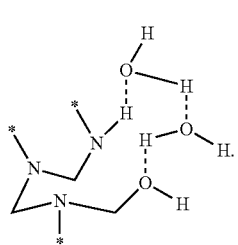

(16)

Divalent bridging groups Q usable for the networks described herein may have at least one 6-carbon aromatic ring. A category of such divalent bridging groups may be represented by the structure of formula (17)

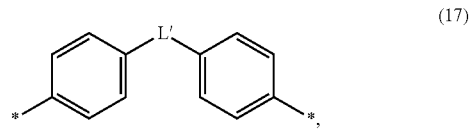

(17)

wherein L' is a divalent bridging group selected from the group consisting of —O—, —S—, —N(R')—, —N(H)—, —R"—, and combinations thereof, wherein R' and R" independently comprise at least 1 carbon. In an embodiment, R' and R" are independently selected from the group consisting of methyl, ethyl, propyl, isopropyl, phenyl, and combinations thereof. Other L' groups include methylene (—CH$_2$—), isopropylidenyl (—C(Me)$_2$-), and fluorenylidenyl:

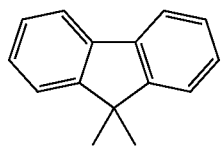

Other divalent bridging groups Q that may be used include:

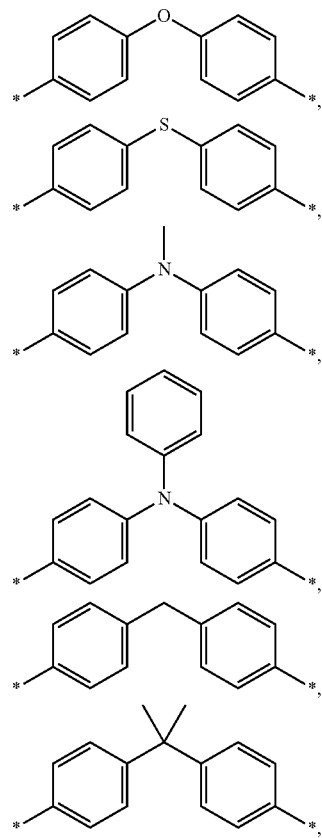

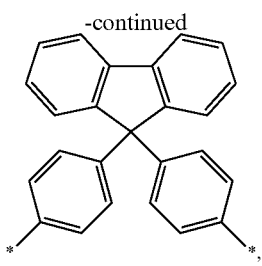

and combinations thereof.

Non-limiting examples of monomers comprising two primary aromatic amine groups that may be used to include the divalent groups described above include 4,4'-oxydianiline (ODA), 4,4'-methylenedianiline (MDA), 4,4'-(9-fluorenylidene)dianiline (FDA), p-phenylenediamine (PD), 1,5-diaminonaphthalene (15DAN), 1,4-diaminonaphthalene (14DAN), and benzidene, which have the following structures:

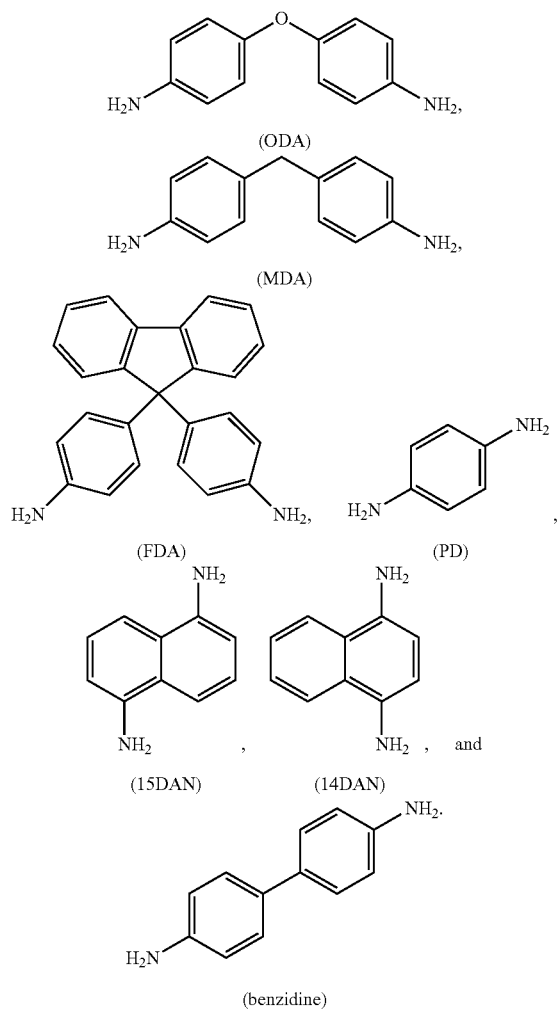

The divalent bridging groups Q may include polymer or oligomer groups. The corresponding precursor may be a diamine-terminated polymer or oligomer, such as a diamine-terminated vinyl polymer, a diamine-terminated polyether, a diamine-terminated polyester, a diamine-terminated star polymer, a diamine-terminated polyaryl ether sulfone, a diamine-terminated polybenzoxazole polymer, a diamine-terminated polybenzimidazole polymer, a diamine-terminated epoxy resin, a diamine-terminated polysiloxane polymer, a diamine-terminated polybutadiene polymer, and a diamine-terminated butadiene copolymer. Diamine-terminated polyethers are commercially available from suppliers such as Huntsman Corp. Diamine-terminated vinyl polymers include long-chain alkyl diamines which may be referred to as polyalkylene diamines, for example polyethylene diamine, polypropylene diamine, and other such polymer diamines. Diamine-terminated vinyl polymers also include long-chain polymer diamines with cyclic and/or aromatic components, such as diamine-terminated polystyrene. The diamine-terminated polymers and oligomers referred to above are commercially available, or may be readily synthesized through well-known reaction pathways.

Usable solvents for the polymerization reaction can be any suitable solvent. Exemplary solvents include dipolar aprotic solvents such as, for example, N-methyl-2-pyrrolidone (NMP), dimethylsulfoxide (DMSO), N,N-dimethylformamide (DMF), N,N-dimethylacetamide (DMA), propylene carbonate (PC), N-cyclohexyl-2-pyrrolidone (CHP), N,N'-dimethylpropyleneurea (DMPU), and propylene glycol methyl ether acetate (PGMEA).

In one example, a PHT network containing ODA bridging groups may have the structure (18)

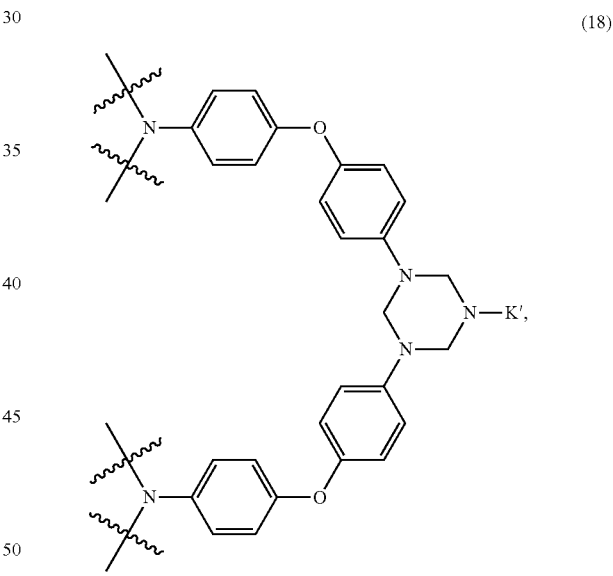

where K' may be any of the aforementioned monomers or bridging groups, including quaternary ammonium moieties or a polymer such as a polyether (i.e., PEG), polyacrylate, polyepoxide, fluoropolymer, or combination thereof.

A precursor mixture for forming the porous polymers described herein may include more than one precursor K'—(NH$_2$)$_x$ and all precursors in the mixture may be divalent or trivalent, or the precursors may be a mixture of monovalent (x=1), divalent (x=2), and trivalent (x=3) species, so long as some divalent or trivalent species are included in the mixture to promote formation of a polymer network.

In general, polymer species K' useful for the reactions described herein may be thermoplastic, thermoset, quasi-thermoplastic, or any combination thereof. Quasi-thermoplastic polymers are those polymers that have a low degree of thermoplasticity derived by partially curing or crosslinking an initially thermoplastic polymer. Including thermoplastic components in the polymer adds toughness and resiliency to the eventual porous material. In general, polymer species K' may have antimicrobial and/or antifouling properties.

aminophenoxy)phenyl)amino)methyl)amino)methyl) amino)methanol. The starting materials are ODA and paraformaldehyde in the presence of N-methyl-2-pyrrolidinone. The reaction mixture is heated gently while mixing to form a gel. The gel is generally a chemical gel, such as an organogel, that includes a polymer dispersed in a solvent. The solvent may be any of the solvents described herein, or

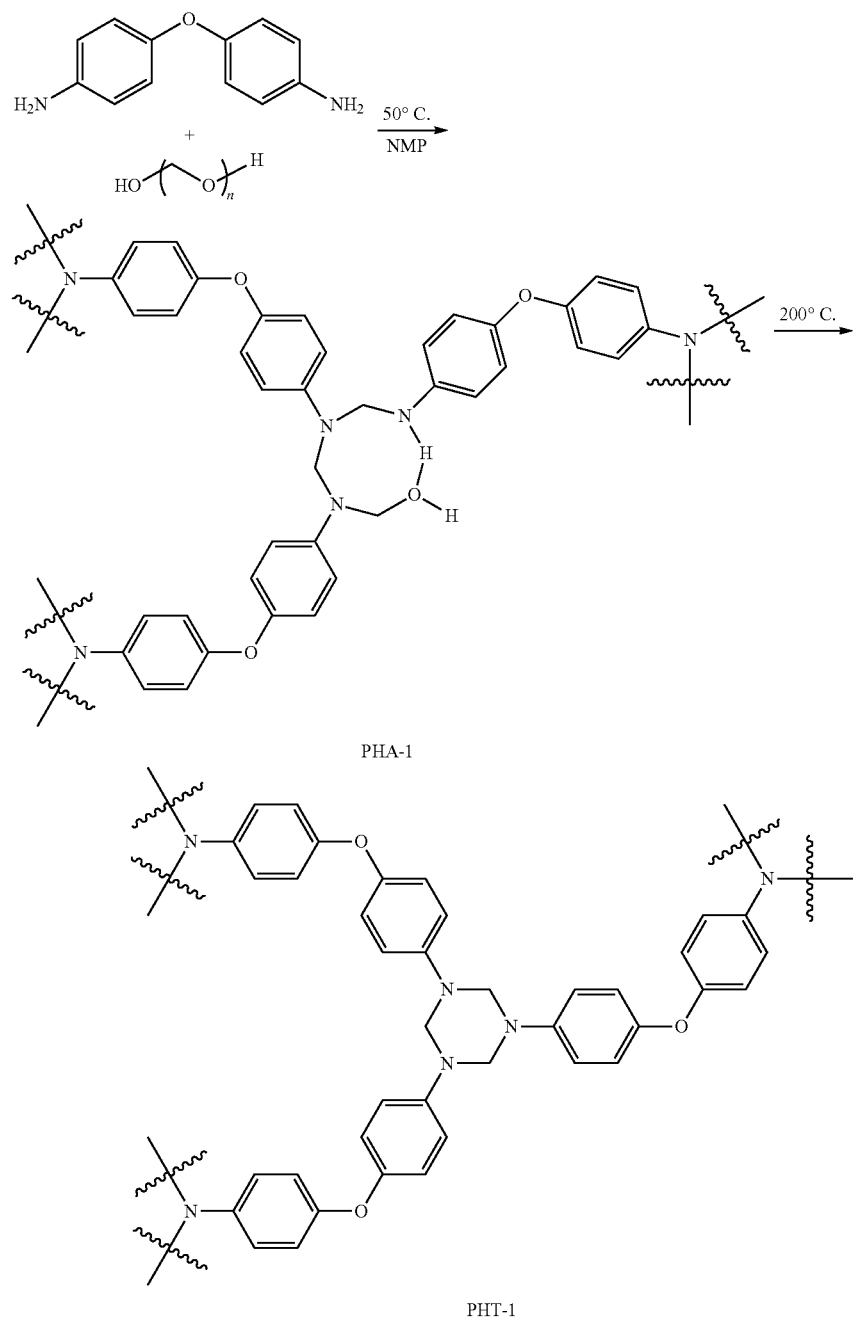

As an example of an embodiment, Scheme 1 shows formation of a porous PHT polymer PHT-1, poly-4,4',4"-(((1,3,5-triazinane-1,3,5-triyl)tris(benzene-4,1-diyl))tris(oxy))trianiline, via PHA-1, poly-((4-(4-aminophenoxy)phenyl)(((4-(4-aminophenoxy)phenyl)(((4-(4- the solvent may be one or more excess precursors described above. The solvent generally maintains separation of polymer chains in the mixture to preserve the gel properties. The reaction may be performed at temperatures of 50° C. to 200° C.

A method of preparing a porous PHT, comprises forming a first mixture comprising i) a monomer, ii) an optional polymer, iii) an optional monovalent monomer, iv) a formaldehyde (i.e., formaldehyde or paraformaldehyde), and v) optionally, a solvent, and heating the first mixture at a temperature of at least 50° C. thereby forming a first mixture comprising PHA. The first mixture may then be heated to a temperature of about 150° C., preferably about 165° C. to about 280° C., thereby forming a second mixture comprising a PHT. The heating time at any of the above temperatures can be about 1 minute to about 24 hours. The PHT polymer may include combinations of both PHA and PHT. The monomer may comprise a bridging group Alternately, a method of preparing a porous PHT comprises forming a first mixture comprising i) a diamine or triamine monomer, optionally comprising either two or three aromatic primary amine groups, ii) an amine terminated precursor, iii) an optional monovalent monomer comprising one aromatic primary amine group, iv) a formaldehyde, and v) a solvent, and heating the first mixture at a temperature of at least 50° C., thereby forming a first mixture comprising PHA. The first mixture can be heated to at least 150° C., preferably about 165° C. to about 280° C., thereby forming a second mixture comprising a PHT. The heating time at any of the above temperatures can be about 1 minute to about 24 hours. The PHT polymer may include combinations of both PHA and PHT. The diamine or triamine monomer may comprise a bridging group.

Alternately, the PHT can be prepared by heating the solution comprising the PHA at a temperature of at least 150° C., preferably about 165° C. to about 280° C., and most preferably at about 200° C. for about 1 minute to about 24 hours.

The bridging groups in Scheme 1 are shown as divalent groups, but as noted above a mixture of divalent and trivalent groups may be present, optionally with some monovalent groups.

Performing the reaction at lower temperatures, for example below about 80° C., forms a polyhemiaminal such as PHA-1. The wavy bonds link the bridging group with a nitrogen atom of another hemiaminal group.

The polymerization reaction proceeds through the hemiaminal stage at low temperatures, and at higher temperatures water is eliminated as the free amine and hydroxyl groups react to close the ring. The polymer formed at the hemiaminal stage may be referred to as a hemiaminal dynamic covalent network (HDCN). Thus, a single polymer chain, network, or mixture may include a mixture of PHAs and PHTs depending on how the reaction is performed. If the reaction is performed for an extended time at a temperature above about 80° C., the polymer will be a polyhexahydrotriazine. If the reaction temperature never exceeds 80° C., the polymer will be mostly, or entirely, polyhemiaminal. If the reaction is performed for a time at a temperature between 50° C. and 80° C., and then continued at a temperature above 80° C. for a limited time, a mixed polymer including hemiaminal and hexahydrotriazine units may be formed, along with any included spacer units.

The reaction forms a gel, which is a polymer dispersed in a solvent. The properties of the gel formed will depend on the reaction performed, the precursors used, and the solvents used. In general, for subsequent operations of the method, the gel has sufficient structural strength to be removed from a reaction vessel and transferred to another vessel.

The gel is subjected to a solvent removal process to form an aerogel. The solvent removal process may be a supercritical $CO_2$ process. The gel is submerged in a fluid that is a mixture of a solvent and liquid $CO_2$. The solvent mixture may be circulated gently, and the temperature of the solvent mixture is maintained so the mixture remains liquid, for example at liquid $CO_2$ temperature. The gel is contacted with the solvent mixture for a time period to allow the solvent mixture to permeate the gel and replace the original solvent. Solvents that may be used with liquid $CO_2$ include alcohols such as methanol and ketones such as acetone. Usable solvents are low-boiling solvents compatible with the gel and miscible with the solvent used to form the gel. In general, solvents boiling at temperatures less than about 80° C. at atmospheric pressure are suited for use in this way.

At this stage, the mixed solvent with liquid $CO_2$ is gradually replaced with liquid $CO_2$. Liquid $CO_2$ is flowed into the vessel containing the gel and the mixed solvent at liquid $CO_2$ temperature, and the mixed solvent is simultaneously withdrawn from the vessel. The overall liquid level in the vessel may be reduced during this operation to speed removal of higher boiling components.

After flowing liquid $CO_2$ into the vessel for a suitable time, for example about three residence times of the liquid volume, the temperature of the mixture is gradually raised to a point above the critical temperature of the $CO_2$, and ultimately to room temperature. The vessel may be sealed during the heating process, or flow of $CO_2$ may be continued. When conditions in the vessel exceed the critical point of $CO_2$, flow of liquid $CO_2$ into the vessel is replaced by flow of supercritical $CO_2$ into the vessel. When a desired pressure is reached in the vessel, gas is vented to maintain the vessel pressure at the desired level. Pressure of the vessel is maintained at a pressure above the critical point of $CO_2$, 7.37 MPa, for example between 7.37 MPa and 9.65 MPa, as the gel is exposed to the supercritical $CO_2$, since the vapor pressure of the solvent removed from the gel may mix with $CO_2$ to form a mixture with critical properties higher than that of pure $CO_2$. Liquid resulting from extraction of the solvent can be drained from the vessel.

After exposure to supercritical $CO_2$ is maintained for a time, flow of supercritical $CO_2$ into the vessel is stopped, and vessel pressure is gradually reduced to ambient pressure by venting $CO_2$ from the vessel. At this time, the vessel contains a dry aerogel.

In an alternate embodiment, solvent is removed from the gel by a vacuum process. The gel is placed in a vessel that is then sealed and provided with vacuum and a flow of a drying gas to maintain a pressure lower than atmospheric pressure for removing solvent from the gel. Maintaining a pressure less than about 500 torr, for example, provides enhanced solvent removal from the aerogel, which would otherwise dry only slowly, or not at all, due to retention of solvent in the spaces between polymer chains in the gel. Heat may be provided to maintain the gel at a temperature up to about 25° C. (i.e. about room temperature) if solvent evaporation cools the gel.

The resulting aerogel is a product of a polymer containing hexahydrotriazine and/or hemiaminal groups linked by the bridging groups described above. The aerogel includes repeating units that have N—C—N bonds linked by bridging groups that may be divalent or trivalent, as described above. The aerogels formed by the methods described herein have improved toughness, but also have the ability to be chemically altered and/or recycled.

An exemplary process of forming a HDCN aerogel uses paraformaldehyde and 4,4'-oxydianiline as precursors. Paraformaldehyde (3.0 equiv., 0.090 g, 3.0 mmol), and 4,4'-oxydianiline (ODA) (0.200 g, 1.0 mmol) were weighed out into a 2-Dram vial equipped with a stir bar inside a $N_2$-filled glovebox and tetrahydrofuran (THF) (2.40 mL, 0.42 M) was added. The reaction mixture was removed from the glovebox, and set up to heat in an oil bath set to 60° C. The reaction was allowed to heat for 12 hours before the solution solidified and residual THF was removed in vacuo. The resulting HDCN material was a white, opaque, hard material that showed porosity/voids by SEM. Such a material can be formed into an aerogel through a solvent replacement process such as that described above.

An exemplary process of forming the PHT aerogel uses formaldehyde and ODA as precursors. In the exemplary process, 0.075 g paraformaldehyde (2.50 equiv., 2.50 mmol), 0.2 g ODA (1.00 mmol), and 1.5 mL NMP (final weight concentration=0.275 g/mL) were weighed out in a 3-dram vial equipped with a stir bar. The vial was capped and transferred into a sand bath. The following thermal treatment may then be used: 50° C. for 1 h, 50° C. to 110° C. over 1 h, 110° C. for 1 h, 110° C. to 200° C. over 1 h, 200° C. for 1 h, and then allow to cool to room temperature. The resulting material can be formed into an aerogel through a solvent replacement process such as that described above.

Porous PHT Polymers Incorporating Metal Ions

The porous polymer network of PHT, PHA, or combinations thereof, can be made antimicrobial by nucleation of bactericidal metal nanoparticles at their surface.

The porous PHT materials (as shown above), including a polymer network of PHT, PHA, or combinations thereof, can be immersed in solutions of metal ions. The metal salts are placed in solution, and the metal salt solutions may contain any suitable solvent, such as dichloromethane, acetonitrile, or mixtures thereof. The metal salts used to make solutions of metal ions can be made from any counterion including triflates, halides, nitrates, sulfates, citrates, and acetates. Examples of metal salts used to make solutions of metal ions include AgOTf or $Zn(OTf)_2$. Such exposure leads to nucleation of metal nanoparticles at the surface of the porous polymer.

An exemplary process of nucleating of metal nanoparticles at the surface of the porous PHT materials uses silver trifluoromethanesulfonate (AgOTf). The porous PHT material was dipped into a silver trifluoromethanesulfonate (AgOTf) solutions (25 mg AgOTf in 1 mL acetonitrile/9 mL dichloromethane) for different durations (1 minute, 1 hour, 3 hours, and 18 hours) at room temperature. The porous PHT material was removed from the solution at the respective exposure time and thoroughly washed with an acetonitrile/dichloromethane mixture (1:9) before drying in a vacuum oven. The porous PHT material may also be rinsed with deionized water instead of the acetonitrile/dichloromethane mixture. While the studies were performed on porous PHT materials that were subjected to silver ions, it should be understood that nucleation can be accomplished using other metal ions such as gold, copper, and zinc.

Table 1 shows the relative atomic concentration (%), as analyzed by X-ray photoelectron spectroscopy (XPS), of the surface of PHT material dipped in a AgOTf solution for 1 minute, 1 hour, 3 hours and 18 hours. High resolution Ag3d and N1s portions of the XPS spectra are shown in FIG. 1. The amount of silver complexed at the surface of the porous PHT materials increased with exposure time to the AgOTf solution. The theoretical maximum silver content for a 1/1 complexation per triazine moiety is Ag/N=⅓. As shown in FIG. 1, the peaks characteristic of the Ag3d orbital increased in intensity with exposure time. The control PHT sample exhibited a broad N1s peak at 399.2 eV (all spectra were referenced to $C(1s)_{max}$=284.8 eV), attributed to N—$C_{arom}$ and N—$CH_2$ bonds, as illustrated in FIG. 1. After 18 h exposure to silver, the most intense signal shifted to 399.6 eV.

TABLE 1

Elemental Compositions of Silver-Incorporated PHTs

| Sample  | C1s  | N1s  | O1s  | Ag3d |
|---------|------|------|------|------|
| Control | 70.9 | 9.4  | 19.4 | 0.0  |
| 1 min   | 70.6 | 10.2 | 16.8 | 0.5  |
| 1 h     | 69.4 | 9.1  | 17.7 | 0.9  |
| 3 h     | 73.4 | 8.5  | 16.2 | 1.0  |
| 18 h    | 72.5 | 8.5  | 14.9 | 3.3  |

The silver-functionalized PHT materials were studied by scanning electron microscopy (SEM). The PHTs materials studied by SEM were dipped in a AgOTf solution for 1 hour, 3 hours and 18 hours. Polydisperse particles with diameters in the 10-100 nm range could be detected at the materials' surface; and the number of particles increased with exposure time of the materials to the AgOTf solution, in good agreement with XPS results.

The presence of nanoparticles (NPs) showed that the interaction of PHT materials with silver was more complex than a simple supramolecular bond between a triazine moiety and a Ag ion. The formation of AgNPs could be explained by the presence of minute amounts of amines at the surface, owing to the aforementioned possible degradation of triazine groups by AgOTf solutions and/or unreacted amines during the PHT synthesis. It is believed that network defects in the PHT films could act as nucleation sites for the formation of AgNPs. Light appears to speed up agglomeration of the silver in the installation of AgNPs at the surface of PHT materials.

A cross-sectional TEM sample of a PHT material dipped in a AgOTf solution for 18 hours was prepared for transmission electron microscopy (TEM) using a focused ion beam (FIB). The sample was coated with evaporated carbon, then platinum was deposited in the FIB over the area of interest. Bright field transmission electron microscopy (BF TEM), high resolution transmission electron microscopy (HR TEM), and high angle annular dark field scanning transmission electron microscopy (HAADF STEM) were performed. Most of the nanoparticles (NPs) were roughly circular with smooth edges, in good agreement with SEM data. As observed by high-resolution TEM and scanning TEM, the NPs exhibited lattice fringes, evidencing at least partial crystallinity.

Figure 2A:
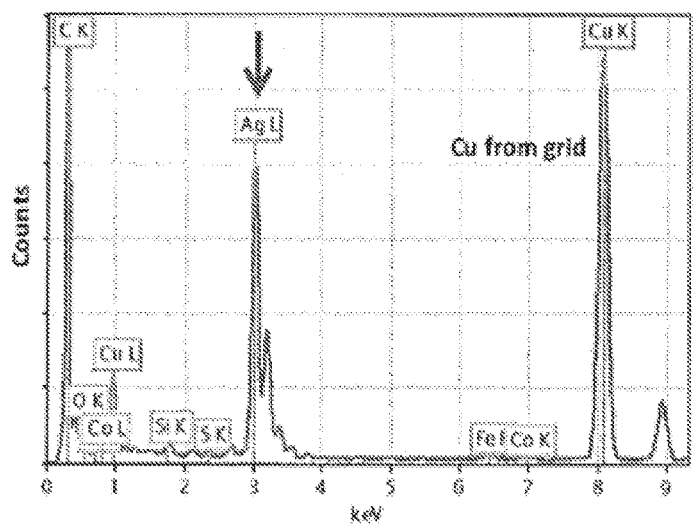
FIG. 2A is an energy-dispersive X-ray spectrograph (EDS) of a nanoparticle found at the surface of the PHT material after immersion in a AgOTf solution for 18 hours.
Figure 2B:
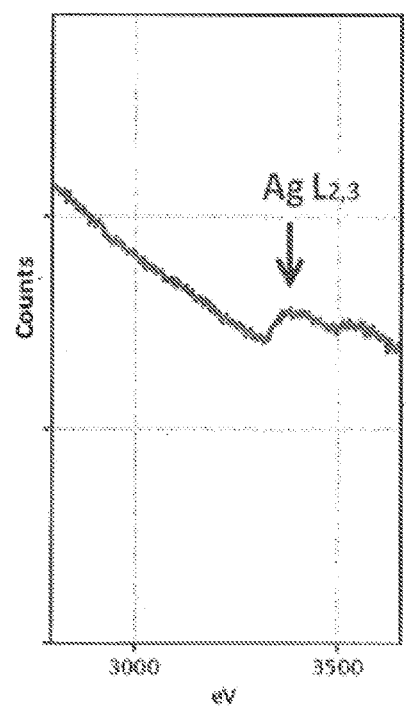
FIG. 2B is an electron energy loss spectrograph (EELS) of a nanoparticle found at the surface of the PHT material after immersion in a AgOTf solution for 18 hours.

The composition of the NPs was analyzed by energy-dispersive X-ray spectroscopy and electron energy loss spectroscopy. FIG. 2A shows an energy-dispersive X-ray spectroscopy (EDS) spectrum of a nanoparticle found at the surface of the PHT material after immersion in a AgOTf solution for 18 hours. FIG. 2B shows an electron energy loss spectroscopy (EELS) spectrum of a nanoparticle found at the surface of the PHT material after immersion in a AgOTf solution for 18 hours. Ag was the main element found in the NPs and the amount of F, if any, was below the detection limit. Therefore, the particles are most likely metallic Ag nucleated from the AgOTf salt solution.

Scheme 2: Porous PHT Incorporating Antifouling Polymer Moieties

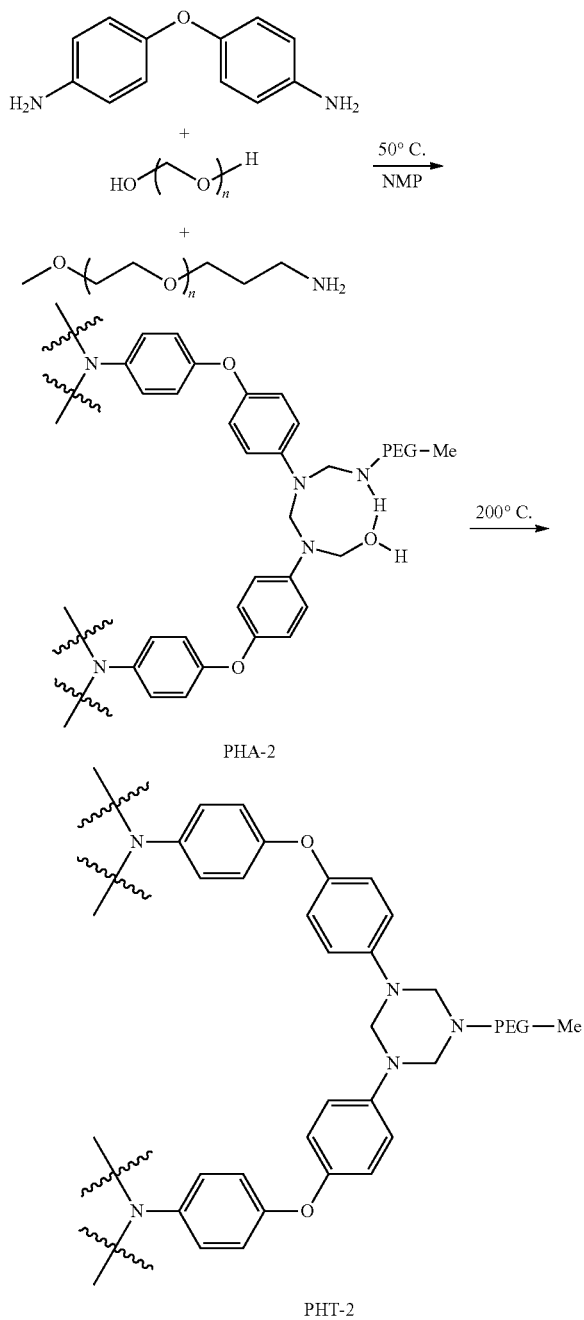

The porous PHT materials (as described above), including a polymer network of PHT, PHA, or combinations thereof, can be modified by an antifouling component.

The nature of the amine used to make a PHA or PHT can modify the thermal properties and solvent resistance of the polymers, for example, by decreasing the crosslinking density. The nature of the amine can also modify the antimicrobial and antifouling properties of the polymer network of PHT, PHA, or combinations thereof. In order to make a PHT or PHA with antifouling properties, antifouling polymers such as polyethers (i.e., PEG), polyacrylates, polyepoxides, fluoropolymers, or combinations thereof, may be used.

A method of preparing a porous PHT with antifouling moieties, comprises forming a first mixture comprising i) an optional diamine or triamine monomer, optionally comprising either two or three aromatic primary amine groups, ii) an amine terminated precursor, which may be a polymer amine and/or diamine, or mixture thereof, iii) an optional monovalent monomer comprising one aromatic primary amine group, iv) a formaldehyde, and v) a solvent, and heating the first mixture at a temperature of at least 50° C., thereby forming a first mixture comprising PHA. The first mixture can be heated to at least 150° C., preferably about 165° C. to about 280° C., thereby forming a second mixture comprising a PHT. The heating time at any of the above temperatures can be about 1 minute to about 24 hours. The diamine or triamine monomer may comprise a bridging group. The PHT polymer may include combinations of both PHA and PHT.

As an example of an embodiment, Scheme 2 shows formation of a porous PHT material incorporating PEG moieties (i.e., monofunctional amino PEG) by reaction of ODA with paraformaldehyde in the presence of N-methyl-2-pyrrolidinone, optionally in the presence of a solvent, at elevated temperature. The reaction mixture is heated gently while mixing to form a gel. The gel is generally a chemical gel, such as an organogel, that includes a polymer dispersed in a solvent. The solvent may be any of the solvents described herein, or the solvent may be one or more excess precursors described above. The solvent generally maintains separation of polymer chains in the mixture to preserve the gel properties. The reaction may be performed at temperatures of 50° C. to 200° C. for about 1 minute to 24 hours. Examples of the final and intermediate product of the reaction are PHT-2, poly-4,4'-(((5-(polyethyleneglycol amino)-1,3,5-triazinane-1,3-diyl)bis(4,1-phenylene))bis(oxy))dianiline, and PHA-2, poly-((4-(4-aminophenoxy)phenyl)(((4-(4-aminophenoxy)phenyl)((polyethyleneglycol amino)methyl)amino)methyl)amino)methanol.

Performing the reaction at lower temperatures, for example below about 80° C., forms a polyhemiaminal (PHA). The wavy bonds link the bridging group with a nitrogen atom of another hemiaminal group. The polymerization reaction proceeds through the hemiaminal stage at low temperatures, and at higher temperatures water is eliminated as the free amine and hydroxyl groups react to close the ring and form the PHT.

An exemplary process of forming a porous PHT material incorporating an antifouling polymer uses a formaldehyde (i.e., formaldehyde or paraformaldehyde), 4,4'-oxydianiline, and monofunctional amino PEG ($M_n$=2,000 g/mol, 20 wt % of total amine content) as precursors to form a PHT in solvent. The reaction is performed at an elevated temperature, optionally in the presence of solvent, from about 1 minute to 24 hours, as generally described above for forming PHT polymer networks. The aerogel of this PHT material may be formed by the process provided above. The PHT material may include combinations of PHA and PHT.

The bridging groups in Scheme 2 are shown as divalent groups, but as noted above, a mixture of divalent and trivalent groups may be present, optionally with some monovalent groups. Although the amino functionalized polymer in Scheme 2 is shown as monofunctional amino PEG, other monofunctional amino polymers may be used including monofunctional amino polyethers, monofunctional amino polyacrylates, monofunctional amino polyepoxides, monofunctional amino fluoropolymers, or combinations thereof. Additionally, the amino functionalized polymer may be monofunctional, bifunctional, or multifunctional, or a mixture thereof.

Scheme 3: Porous PHT Polymers Incorporating Cationic Moieties
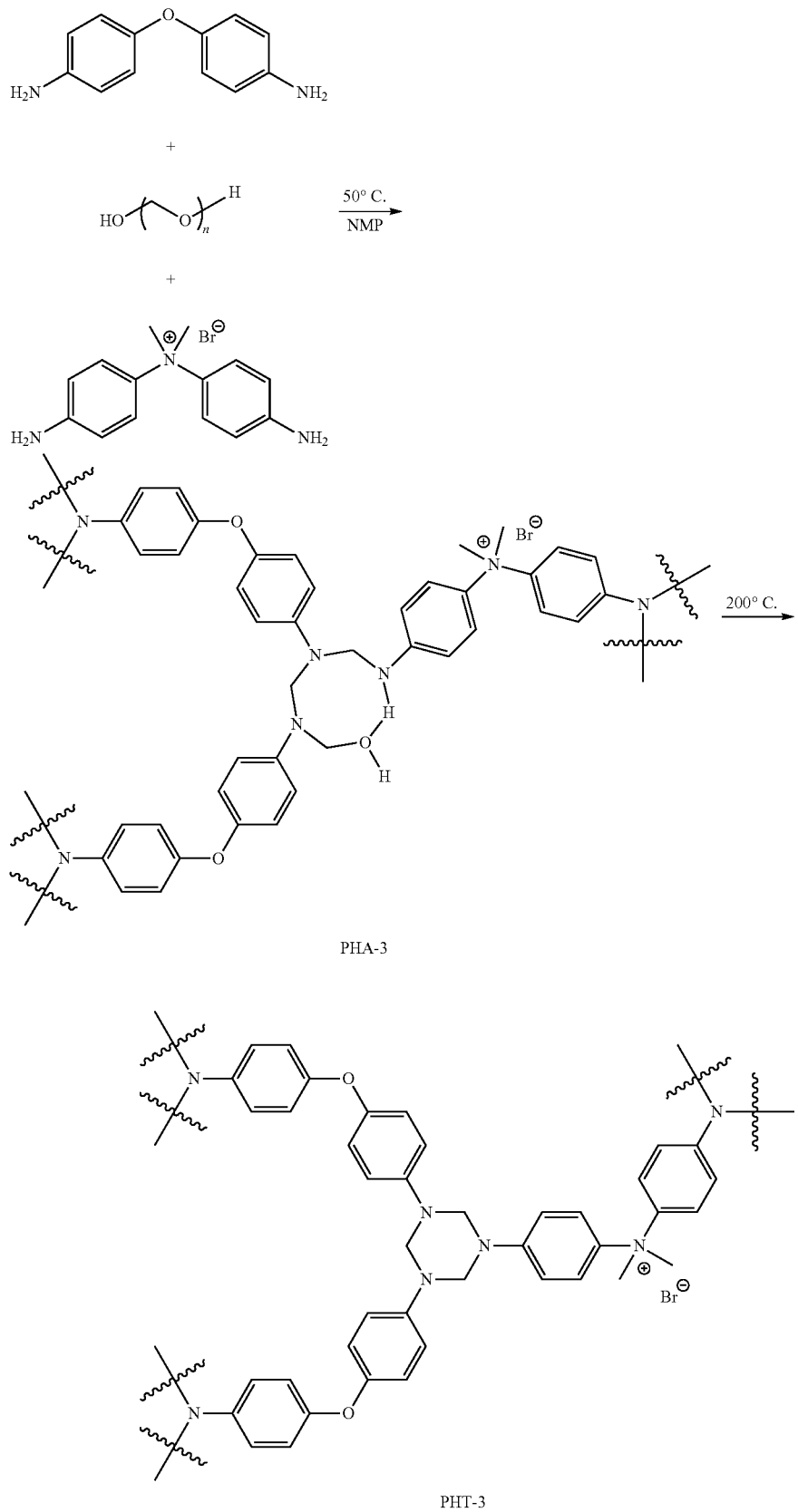
PHA-3
PHT-3

The porous polymer network of PHT, PHA, or combinations thereof, can exhibit antimicrobial activity by incorporating cationic moieties into the chemical network of the polymer material.

As an example of an embodiment, Scheme 3 shows formation of the porous PHT incorporating cationic moieties. The cationic moieties may include quaternary ammonium-containing amines, including quaternary ammonium-containing diaromatic amine, such as 4-amino-N-(4-aminophenyl)-N,N-dimethylbenzenaminium bromide. Quaternary ammonium-containing diaromatic amines may be prepared by quaternization of 2-(dimethylamino)ethyl acrylate with 2-chloroethyl acrylate in any suitable solvent, including THF, followed by conjugate addition with 4-aminothiophenol in any suitable solvent including NMP. The product may be used without further purification for the synthesis of the PHT materials.

A method of preparing a porous PHT having cationic species, may comprise forming a first mixture comprising i) an optional diamine or triamine monomer, optionally comprising either two or three aromatic primary amine groups, ii) an amine terminated precursor, iii) an optional monovalent monomer comprising one aromatic primary amine group, iv) a formaldehyde, and v) a solvent, and heating the first mixture at a temperature of at least 50° C., thereby forming a first mixture comprising PHA. The first mixture can be heated to at least 150° C., preferably about 165° C. to about 280° C., thereby forming a second mixture comprising a PHT. The heating time at any of the above temperatures can be about 1 minute to about 24 hours. The diamine or triamine monomer may comprise a bridging group. The PHT polymer may include combinations of both PHA and PHT.

The quaternary ammonium-containing diamine, 4-amino-N-(4-aminophenyl)-N,N-dimethylbenzenaminium bromide may be synthesized by the following exemplary process. 2.00 g 2-(dimethylamino)ethyl acrylate (14.0 mmol) and 2.26 g 2-chloroethyl acrylate (16.8 mmol) were refluxed with hydroquinone in 2 mL THF for 36 hours. The volatile were removed under vacuum (4 h), and the product was stored in the fridge. 1.06 g of crude product (3.8 mmol) were stirred with 0.94 g 4-aminothiophenol (7.5 mmol) in 4 mL NMP until complete disappearance of the acrylate moieties (as checked by NMR, approx. 18 h). The product was extensively washed with acetone by trituration and dried under vacuum overnight, yielding a brownish paste (purity ~95% by NMR). $^1$H NMR (400 MHz, DMSO-$d_6$): δ (ppm) 7.10 (d, 4H, J=8.4 Hz, $CH_{arom}$), 6.56 (d, 4H, J=8.4 Hz, $CH_{arom}$), 4.50 (br, 4H, —O—$CH_2$—$CH_2$—$N^+$), 3.77 (br, 4H, —O—$CH_2$—$CH_2$—$N^+$), 3.38 (s, 6H, —$N^+(CH_3)_2$), 2.90 (t, 4H, —S—$CH_2$—$CH_2$—CO), 2.54 (t, 4H, —S—$CH_2$—$CH_2$—CO).

As shown in Scheme 3, diamines carrying a quaternary ammonium moiety can be incorporated into the PHA/PHT network by reaction or a quaternary diamine or triamine, as described above, with ODA and a formaldehyde (formaldehyde or paraformaldehyde), optionally in the presence of a solvent, at elevated temperatures. The reaction mixture is heated gently while mixing to form a gel. The gel is generally a chemical gel, such as an organogel, that includes a polymer dispersed in a solvent. The solvent may be any of the solvents described herein, or the solvent may be one or more excess precursors described above. The solvent generally maintains separation of polymer chains in the mixture to preserve the gel properties. The reaction may be performed at temperatures of 50° C. to 200° C. for about 1 minute to 24 hours. The aerogel of this porous PHT material may be formed by the process provided above. The PHT material may include combinations of PHA and PHT. The bridging groups in Scheme 3 are shown as divalent groups, but as noted above, a mixture of divalent and trivalent groups may be present, optionally with some monovalent groups. Examples of the final and intermediate products of the reaction are PHT-3, poly-N-(4-aminophenyl)-N-(4-(3,5-bis(4-(4-aminophenoxy)phenyl)-1,3,5-triazinan-1-yl)phenyl)-N-methylmethyliumaminium bromide, and PHA-3, poly-4-amino-N-(4-((((4-(4-aminophenoxy)phenyl)(((4-(4-aminophenoxy)phenyl)(hydroxymethyl)amino)methyl)amino)methyl)amino)phenyl)-N,N-dimethylbenzenaminium bromide.

Performing the reaction at lower temperatures, for example below about 80° C., forms a polyhemiaminal. The wavy bonds link the bridging group with a nitrogen atom of another hemiaminal group. The polymerization reaction proceeds through the hemiaminal stage at low temperatures, and at higher temperatures water is eliminated as the free amine and hydroxyl groups react to close the ring and form the PHT.

The PHT, PHA, or mixed PHT/PHA polymers described above having quaternary amine components may be formed into aerogels using the solvent replacement process described above.

Porous PHT Polymers Incorporating Antimicrobial and Antifouling Moieties

In another embodiment, the porous PHT polymers may incorporate both antimicrobial (i.e., metal ions and/or cationic moieties) and antifouling moieties such as polyethers, polyacrylates, polyepoxides, fluoropolymers, or combinations thereof. In such cases, the starting materials for the reaction would be altered, though performed in a similar fashion as described above. The porous polymer having antimicrobial and antifouling components may contain PHT, PHA, or a mixed PHT/PHA polymer. Following formation of a polymer material having quaternary ammonium salts and/or antifouling polymers incorporated into the chemical network, the polymer material may be immersed in a metal ion solution, as described above. The polymer material may also be an aerogel, as described above.

In an exemplary process, a method of preparing a porous PHT having antimicrobial and antifouling components, may comprise forming a first mixture comprising i) an optional diamine or triamine monomer, optionally comprising either two or three aromatic primary amine groups, ii) an amine terminated precursor, iii) an optional monovalent monomer comprising one aromatic primary amine group, iv) an optional cationic species, v) a formaldehyde, and vi) a solvent, and heating the first mixture at a temperature of at least 50° C., thereby forming a first mixture comprising PHA. The first mixture can be heated to at least 150° C., preferably about 165° C. to about 280° C., thereby forming a second mixture comprising a PHT. The heating time at any of the above temperatures can be about 1 minute to about 24 hours. The porous PHT polymer may include combinations of both PHA and PHT. The diamine or triamine monomer may comprise a bridging group. The porous polymer having antimicrobial and antifouling components may be immersed in a metal ion solution, as described above.

In an embodiment, a porous polymer is provided. The porous polymer comprises a plurality of hexahydrotriazine units, hemiaminal units, or a combination thereof, forming a polymer network; and an antifouling component covalently linked to the polymer network, an antimicrobial component chemically linked to the polymer network, or a combination thereof "Chemically linked" includes both covalent bonding and non-covalent bonding. For example, incorporating an antifouling polymer (such as PEG), a quaternary ammonium moiety, or a combination of both, into the polymer network is accomplished via covalent bonding hexahydrotriazine units, hemiaminal units, or a combination thereof. Non-covalent bonding includes nucleation of metal nanoparticles at the surface of the porous polymer, for example, the complexation of silver particles with the triazine moiety.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A porous polymer composition, comprising:
    a plurality of hexahydrotriazine units, hemiaminal units, or a combination thereof, forming a polymer network; and
    an antimicrobial component chemically linked to the polymer network by at least one of a chemical bond and a non-covalent bond, the antimicrobial component comprising a quaternary ammonium salt.

2. The porous polymer composition of claim 1, wherein the porous polymer composition is an aerogel.

3. The porous polymer composition of claim 1, further comprising an amino functionalized polymer covalently linked to the polymer network.

4. The porous polymer composition of claim 1, further comprising an amino PEG covalently linked to the polymer network.

5. An aerogel comprising a porous polymer composition, the porous polymer composition comprising:
    a plurality of hexahydrotriazine units, hemiaminal units, or a combination thereof, forming a polymer network; and
    at least one of (a) an antifouling component covalently bonded to the polymer network, and (b) an antimicrobial component chemically linked to the polymer network by at least one of a chemical bond and a non-covalent bond.

6. The aerogel of claim 5, wherein the antimicrobial component comprises metal ions, quaternary ammonium salts, or a combination thereof.

7. The aerogel of claim 5, wherein the antifouling component comprises an amino functionalized polymer.

8. The aerogel of claim 5, wherein the antifouling component is an amino PEG.

9. A porous polymer composition, comprising:
    a plurality of hexahydrotriazine units, hemiaminal units, or a combination thereof, forming a polymer network;
    an antifouling component covalently bonded to the polymer network; and
    an antimicrobial component chemically linked to the polymer network by at least one of a chemical bond and a non-covalent bond, wherein the antimicrobial component comprises quaternary ammonium salts.

10. The porous polymer composition of claim 9, wherein the porous polymer composition is an aerogel.

11. The porous polymer composition of claim 9, wherein the antifouling component comprises an amino functionalized polymer.

12. The porous polymer composition of claim 9, wherein the antifouling component is an amino PEG.

* * * * *